(12) United States Patent
Tokuda et al.

(10) Patent No.: US 8,156,789 B2
(45) Date of Patent: Apr. 17, 2012

(54) GAS SENSOR CHIP AND GAS SENSOR PROVIDED THEREWITH

(75) Inventors: Tomohisa Tokuda, Tokyo (JP);
Shinsuke Matsunaga, Tokyo (JP);
Yoshiyuki Nakazaki, Tokyo (JP);
Kouichirou Hotta, Tokyo (JP)

(73) Assignee: Yamatake Corporation, Tokyo (JP)

( * ) Notice: Subject to any disclaimer, the term of this patent is extended or adjusted under 35 U.S.C. 154(b) by 539 days.

(21) Appl. No.: 12/365,262

(22) Filed: Feb. 4, 2009

(65) Prior Publication Data
US 2009/0193872 A1    Aug. 6, 2009

(30) Foreign Application Priority Data
Feb. 5, 2008 (JP) .................................. 2008-025783

(51) Int. Cl.
*G01N 25/00* (2006.01)
(52) U.S. Cl. .................. 73/25.01; 73/23.2; 73/23.25
(58) Field of Classification Search ................. 73/25.01, 73/23.2, 23.25
See application file for complete search history.

(56) References Cited

FOREIGN PATENT DOCUMENTS
JP        08-226909 A    9/1996

*Primary Examiner* — Hezron E Williams
*Assistant Examiner* — Rodney T Frank
(74) *Attorney, Agent, or Firm* — McDermott Will & Emery LLP

(57) ABSTRACT

To provide a gas sensor chip, and a gas sensor provided therewith, capable of producing stable output characteristics over an extended period of time even when installed in a harsh environment such as a boiler smokestack carrying exhaust gasses. There is a backside structure wherein a catalyst carrier that contacts a gas to be measured is disposed on one side of a thermal conductor, a temperature sensing portion is disposed in a location that does not contact the gas to be measured, on the other side of the thermal conductor, and the temperature sensing portion measures the temperature corresponding to the temperature of the catalyst carrier through the thermal conductor, to enable the sensing of the amount of flow over an extended period of time without the temperature sensing portion being negatively affected by the gas to be measured.

1 Claim, 6 Drawing Sheets

GAS SENSOR CHIP AND GAS SENSOR PROVIDED THEREWITH

CROSS-REFERENCE TO RELATED APPLICATION

The present application claims priority under 35 U.S.C. §119 to Japanese Patent Application No. 2008-025783 filed on Feb. 5, 2008. The content of the application is incorporated herein by reference in its entirety.

FIELD OF TECHNOLOGY

The present invention relates to a small gas sensor chip of a contact combustion type, having a superior durability, and to a gas sensor provided therewith.

BACKGROUND

Contact combustion-type gas sensors for detecting quantities of constituent carbon monoxide, which is a non-combusted gas in, for example, and exhaust gas, having high sensitivity to only non-combusted gasses such as carbon monoxide, have been known conventionally. (See, for example, Japanese Unexamined Patent Application Publication H8-226909 ("JP '909") (Pages 3-4 and FIG. 1)).

In the contact combustion type gas sensor set forth in JP '909, the gas detecting element and supplementary elements that structure a bridge circuit are supported on metal pins that are secured by penetrating through an insulating base, and these elements are covered by a cap. The gas sensing element includes a temperature measuring resistor and an oxidation combustion catalyst layer that is coated onto the temperature measuring resistor, where the oxidation combustion catalyst layer is made from a fine powder of an a ferric oxide carrying a gold catalyst, and an alumina powder carrying a platinum catalyst and a palladium catalyst.

Additionally, the temperature measuring resistor and the oxidation combustion catalyst layer that is coated thereon are exposed directly in the exhaust gas that includes the non-combusted gas, for example, to convert the increase in temperature of the oxidation combustion catalyst layer concomitant with the combustion of the non-combusted gas into a change in the resistance value of the temperature measuring resistor, so as to detect the quantity of the non-combusted gas constituent through a bridge circuit that includes supplementary elements.

In the contact combustion-type gas sensor such as set forth in JP '909 there are shortcomings such as the overall size being large, the sensor itself tending to increase costs, and there being constraints on the location of installation. Because of this, in recent years extremely small contact combustion-type gas sensors that use MEMS (Micro-Electromechanical Systems) technology have been used.

In a gas sensor such as set forth above, there are cases wherein gasses that are a hazardous environment to the sensor structural materials have been selected as being subject to measurement, and there has also been, for example, dust and the like, causing service life of the sensor to be reduced by this type of measurement environment. The shorter the service life of the sensor, the more frequent the maintenance (or the more frequently the sensor is replaced), producing a problem in terms of ensuring operation and in terms of operating costs.

The present invention considers the effect on the service life of the catalyst layer and the temperature measuring resistor being in direct contact, and provides a gas sensor chip, and a gas sensor provided therewith, that solves this problem to enable stabilized output characteristics over an extended period of time.

SUMMARY

In order to solve the problem set forth above, the gas sensor chip of the present invention is characterized as being:
a catalyst carrier that contacts a gas to be measured is disposed on one side of a thermal conductor;
a temperature sensing portion is disposed on the other side of the thermal conductor in an area that does not contact the gas to be measured; and
the temperature sensing portion measures a temperature corresponding to the temperature of the catalyst carrier through the thermal conductor.

Because the gas sensor chip set forth above has a so-called backside structure wherein the catalyst carrier that catalyzes the gas to be measured and the temperature sensing portion that does not contact the gas are disposed on opposite sides in this way, with a thermal conductor interposed therebetween, the temperature sensing portion is able to detect the gas flow over an extended period of time without being adversely affected by the gas being measured.

Furthermore, the gas sensor chip of the present invention is characterized comprising:
a base substrate made from silicon;
a temperature measuring resistor disposed on one surface of the base substrate and an electrode conducting electrically thereto;
a recessed portion for forming a thin wall portion of the base substrate on the opposite side of the base substrate facing the temperature measuring resistor, in the interval of the temperature measuring resistor;
a porous silicon layer is formed on at least the surface of the thin walled portion of the inner surface of the recessed portion;
an oxidation combustion catalyst that is supported by the porous silicon layer; and
a glass mount that is connected to the temperature measuring resistor side of the base substrate; wherein
a gas flows on the side of the base substrate that is opposite from the surface in which the temperature measuring resistor is formed.

The gas sensor chip set forth above, having this type of structure, causes the temperature measuring resistor to be formed on the side of the base substrate that is opposite from the side wherein the gas flows. Because of this, in the particular case of measuring non-combusted gas in exhaust gasses that flow through the smokestack of a boiler, the temperature sensing portion does not come in contact with the exhaust gas, and thus no degradation is produced such as corrosion of the electrodes or shorting of the interconnections of the temperature sensing portions such as described above. Because of this, even when using extremely small gas sensor chips based on MEMS technology, it is still possible to detect the quantity of the carbon monoxide constituent over an extended period of time with stability.

As a result, it becomes possible to optimize the combustion efficiency of the combustion device through feeding back to a combustion control device of the boiler, for example, the quantity of the non-combusted gas constituent in the exhaust gasses, and to detect immediately any degradation in the performance of the boiler itself.

Additionally, the gas sensor can include two of the gas sensor chips set forth above, disposed aligned through an identical surface of a sensor supporting member being bonded to the glass mount; having electrode lead portions formed extending in each of the gas sensor chips to the side of the base substrate that is opposite from the side wherein the gas flows; wherein one of the sensor chips is provided on the sensor supporting member in a state wherein the oxidation combustion catalyst is included in the porous layer, and the other sensor chip is provided on the sensor supporting member in a state wherein the oxidation combustion catalyst is not included in the porous layer.

The gas sensor above enables a comparison of the outputs of the temperature measuring resistors of the gas sensor chip that is provided with the oxidation combustion catalyst and the gas sensor chip that is not provided with the oxidation combustion catalyst, to thereby enable the detection of only the change in temperature that is due to the combustion of the non-combusted gas that is included in the exhaust gas, without being affected by changes in temperature of the exhaust gas itself or changes in the ambient temperature. This enables a more accurate detection of the quantity of the non-combusted gas constituent in the exhaust gas.

Additionally, the durability of the gas sensor chip itself is increased by the measurement resistor not coming into direct contact with the gas, enabling a reduction in the frequency of maintenance of the gas sensor.

The present invention enables the provision of a gas sensor chip, and of a gas sensor provided therewith, capable of providing stable output characteristics over an extended period of time, even when equipped in a harsh environment such as a boiler smokestack carrying exhaust gasses.

DETAILED DESCRIPTION

Figure 1:
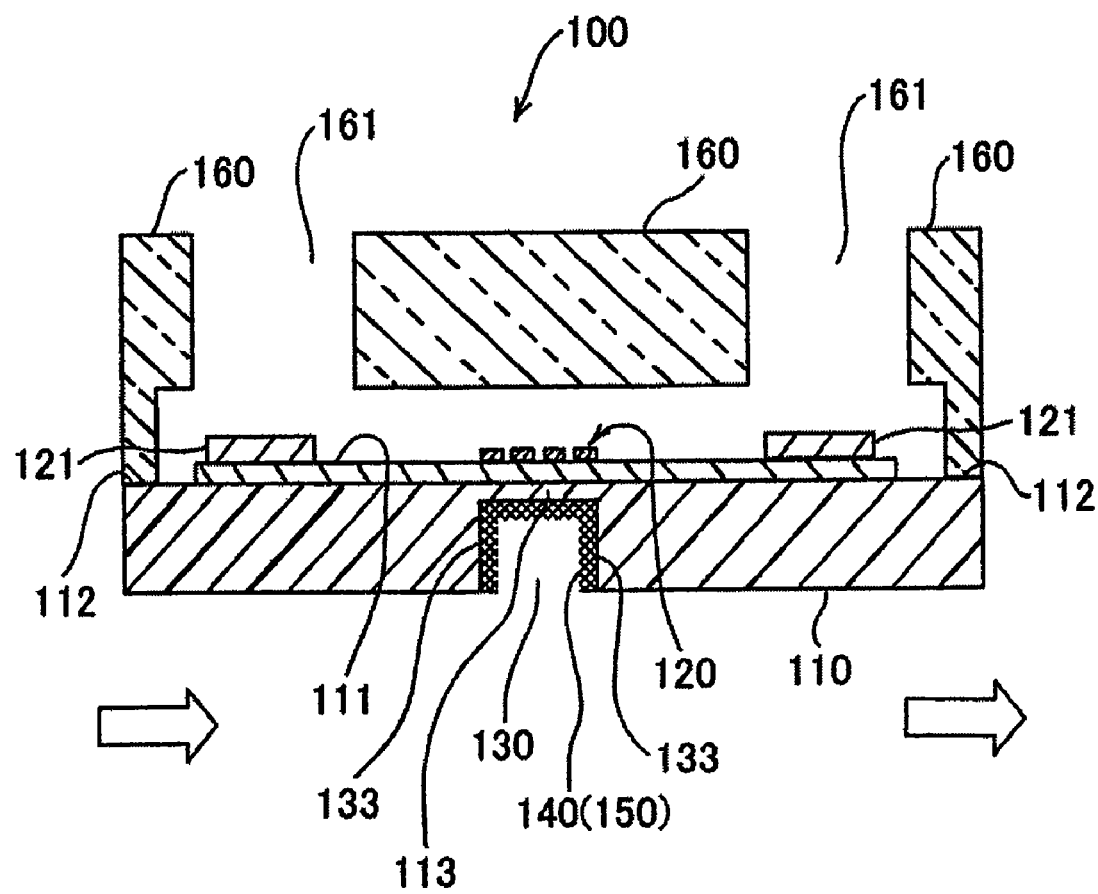
FIG. 1 is a cross-sectional diagram of a gas sensor chip according to one example, along the perpendicular direction relative to the surface of the base substrate in which the temperature measuring resistor is fabricated.

A gas sensor chip 100, and a gas sensor 10 provided therewith, which are one example of embodiment according to the present invention, will be explained in detail below referencing the figures. The gas sensor chip 100 that is one embodiment of the present invention will be explained first. FIG. 1 is a cross-sectional diagram illustrating the gas sensor chip 100 according to one example of embodiment according to the present invention, along the direction that is perpendicular to the surface of the base substrate 110 wherein a temperature measuring resistor is fabricated.

This gas sensor chip 100, as illustrated in FIG. 1, comprises a base substrate 110, a temperature measuring resistor 120 that is patterned in the surface on one side of the base substrate 110, a recessed portion 130 that is formed on the opposite side of the base substrate 110 facing the temperature measuring resistor 120, a porous silicon layer 140 provided on the inside surface of the recessed portion 130, an oxidation combustion catalyst 150 that is supported on the porous silicon layer 140, and a glass mount 160 that is connected to the temperature measuring resistor side of the base substrate 110. The gas flows on the side of the base substrate 110 opposite from that of the temperature measuring resistor 120, or in other words, on the side having the surface wherein the recessed portion 130 is formed. (See the white arrow in FIG. 1.)

The base substrate 110 is made out of a silicon substrate, where a silicon nitride (SiN) layer 111 is formed on one surface as an electrically insulating layer, and a temperature measuring resistor 120 made from platinum (Pt) is patterned into the center portion on the surface on top of the silicon nitride layer 111. Furthermore, electrode pads 121 made from gold (Au) are formed on both sides of the surface on top of the silicon nitride layer 111 so as to lie on either side of the temperature measuring resistor 120.

Note that this temperature measuring resistor 120 is a temperature measuring resistor of a self-heating type that also acts as the heater, making it possible to increase the temperature of the catalyst carrying portion to 280° C. in the normal ambient gas within the boiler smokestack through applying a specific electric current.

Additionally, the platinum interconnection pattern (not shown) is formed extending from the temperature measuring resistor 120 to the electrode pads 121, and the temperature measuring resistor 120 and the interconnection pattern are covered by an insulating layer made from a silicon nitride layer, not shown. Note that springs 126, provided at the tips of electrode lead pins 125, set forth below, press against the electrode pads 121, so as to produce an electric current in the temperature measuring resistor 120 through the electrode lead pins 125.

Furthermore, at both end portions of the silicon nitride layer 111 on the base substrate, the silicon substrate is exposed directly, and the glass mount 160 is anodically bonded to a portion of these bonding areas 112. The glass mount 160 is made from borosilicate glass such as Pyrex® glass, and holes 161 for the electrode leads are formed in the portions corresponding to the electrode pads 121, with the balance covering the temperature measuring resistor 120, which is formed on the silicon nitride layer, with a predetermined gap therefrom.

A recessed portion 130, having an opening portion of a size corresponding to the temperature measuring resistor 120 is formed on the surface of the base substrate 110 on the side opposite from the temperature measuring resistor 120. The bottom surface of this recessed portion 130 (the top surface in the figure) forms a thin wall portion 113 of the base substrate 110 corresponding to the area wherein the temperature measuring resistor 120 is formed.

The thin wall portion 113 is a thermal conductor for conducting the heat that is generated by the oxidation combustion catalyst 150, described below, to the temperature measuring resistor 120, and fulfills the role as the thermal conductor for conducting, to the temperature measuring resistor 120, the temperature that corresponds to the temperature of the porous silicon layer 140 that serves as the catalyst carrier, and also, insofar as is possible, does not conduct this heat to the surrounding base substrate 110.

The inside surface of the recessed portion 130, that is, the thin wall portion 113 corresponding to the temperature measuring resistor 120 and the porous silicon layer 140 formed on the side wall surface 133 of the recessed portion 130, fulfills the role as the carrier for the oxidation combustion catalyst 150.

The oxidation combustion catalyst 150 that is carried by the porous silicon layer 140 is supported by the porous silicon layer 140 through impregnating a catalyst fluid that contains platinum (Pd) into the porous silicon layer 140 and then sintering.

Additionally, in the present example of the gas that contains carbon dioxide, which is a non-combusted gas, in the boiler exhaust gas is caused to flow along the surface on the side of the base substrate 110 that is opposite of the surface wherein the temperature measuring resistor 120 is formed.

Figure 2:
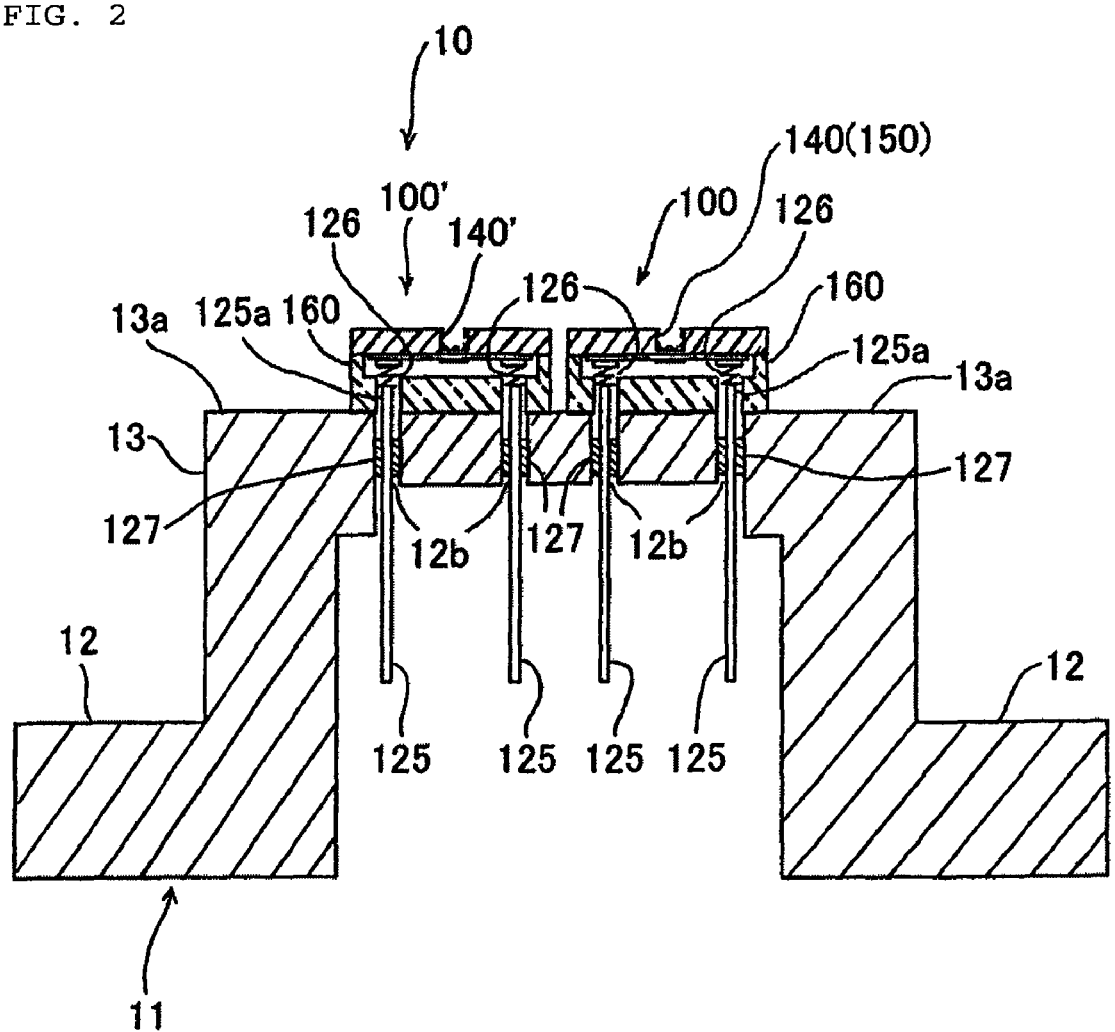
FIG. 2 is a cross-sectional diagram of a gas sensor according to the present example, provided with the gas sensor chip illustrated in FIG. 1.

A gas sensor 10 provided with this gas sensor chip 100 will be explained next. FIG. 2 is a cross-sectional diagram illustrating schematically the overall structure of the gas sensor 10. The gas sensor 10 is provided with a sensor supporting member 11 and two gas sensor chips 100 and 100' that are disposed lined up on the same surface of the sensor supporting member 11.

The individual gas sensor chips 100 and 100' are disposed by the respective glass mounts 160 being adhered to the sensor supporting member 11. Additionally, in one of the gas sensor chips 100, the oxidation combustion catalyst 150 is carried on the porous silicon layer 140, as described above, but the other gas sensor chip 100' is disposed on the sensor supporting member 11 in a state wherein no oxidation combustion catalyst is supported by the porous silicon layer 140'. Note that this is also true for the other structures of the two gas sensor chips 100 and 100'.

The gas sensor chip 100' is disposed on the sensor supporting member 11 in a state wherein no oxide combustion catalyst is supported on the porous silicon layer 140', so the thin film portion of the other gas sensor chip 100' corresponding to the thin wall portion 113 of the one gas sensor chip 100 fulfills the role of being a thermal conductor for conducting, to the temperature measuring resistor 120, the temperature corresponding to the temperature of the porous silicon layer 140' that serves as the catalyst carrier.

The sensor supporting member is made out of, for example, stainless steel (SUS), and, as illustrated in FIG. 2, comprises a base portion 12 and a protruding portion 13 that protrudes from the base portion 12, where the gas sensor chip is adhered and secured to the top surface 13a of the protruding portion 13 with the glass mount 160 interposed herebetween. Electrode lead holes 12b for the electrode lead pins 125 to lead out from the electrode pads 121 of the gas sensor chips 100 and 100' are formed in a portion of the protruding portion 13, where the electrode lead pins 125 pass through these electrode lead holes 12b to guide the electrode lead pins 125 in the recessed portion on the side of the sensor supporting member 11 that is opposite from the side wherein the gas sensor chips are disposed.

Electrically conductive springs 126 are provided at gas sensor chip side end portions 125a of the electrode lead pins 125 to make reliable electrical contact between the gas sensor chip side end portions 125a of the electrode lead pins 125 and the electrode pads 121 of the gas sensor chips 100 through the elastic force of these springs 126. Additionally, the electrode lead pins 125 are supported in intimate contact with the electrode lead holes 12b through hermetic seals 127. Note that the hermetic seals 127 also fulfill the role of achieving electrical insulation between the electrode lead pins 125 and the surrounding sensor supporting member 11.

Electric wires, not shown, are connected to the tips of these four electrode lead pins 125, and along with providing electric power to the temperature measuring resistors 120, form a known Wheatstone bridge circuit in cooperation with the temperature measuring resistors 120, so as to be able to output, as a voltage value, a differential between the temperature of the gas sensor chip 100 that has the oxidation combustion catalyst 150 and the temperature of the gas sensor chip 100' that does not have the oxidation combustion catalyst 150.

The operation of the gas sensor 10 that is provided with these gas sensor chips 100 and 100' will be explained next.

Figure 3:
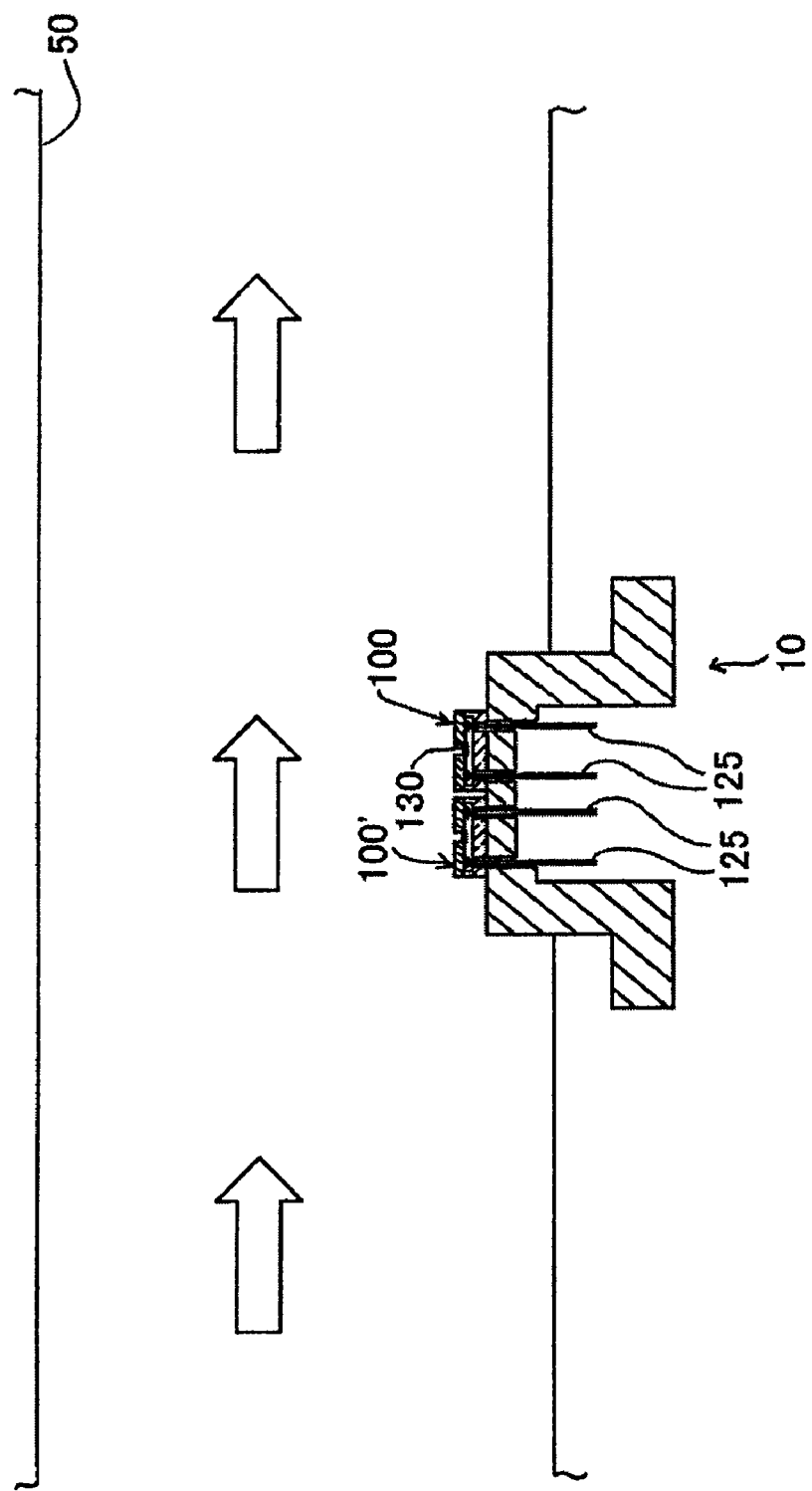
FIG. 3 is a cross-sectional diagram illustrating the state wherein the gas sensor illustrated in FIG. 2 is installed in a boiler smokestack.
Figure 4:
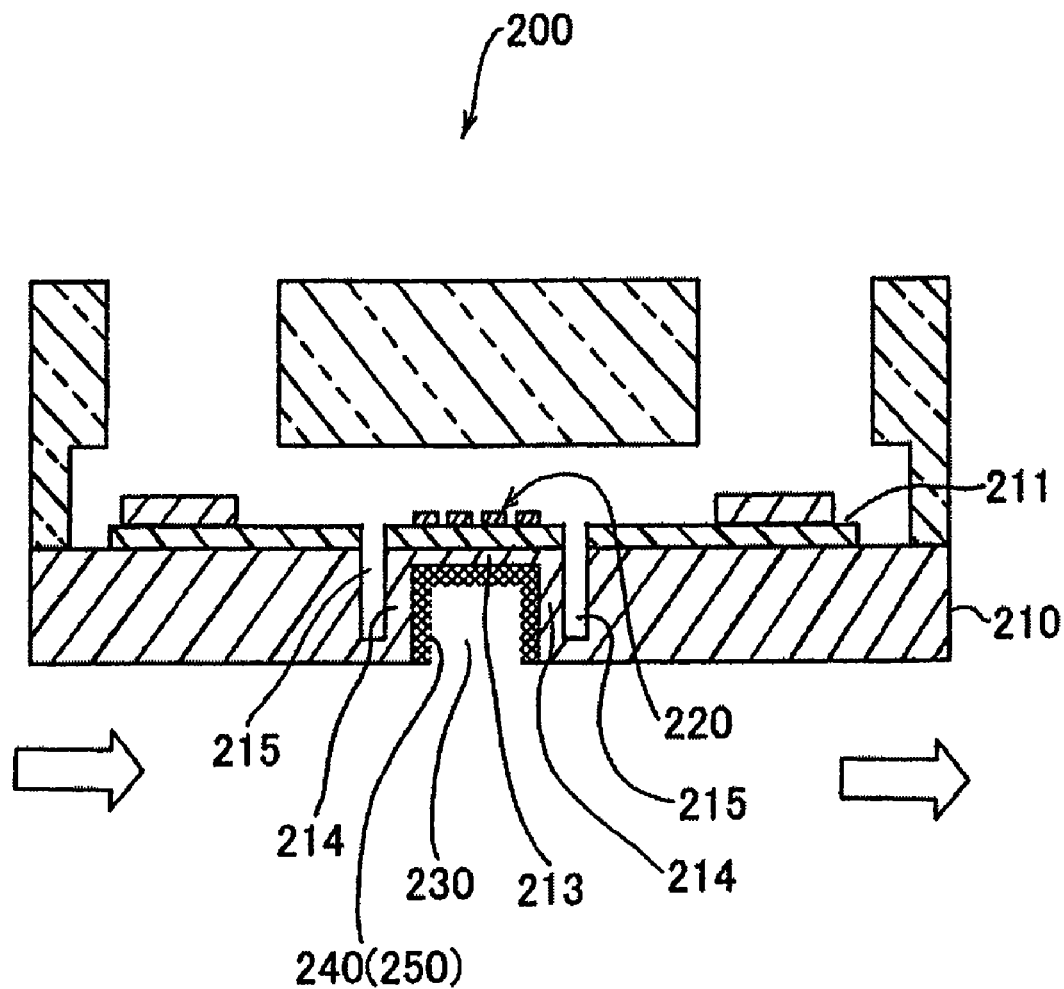
FIG. 4 is a cross-sectional diagram illustrating a modified example of the gas sensor chip illustrated in FIG. 1.

FIG. 3 illustrates a state wherein the gas sensor 10 set forth above is installed in a smokestack 50 that carries the exhaust gas of a boiler (not shown). Note that to facilitate ease in understanding the explanation, in FIG. 3 the gas sensor 10 is drawn quite large relative to the smokestack 50. However, in actuality the gas sensor chips 100 and 100' are manufactured using MEMS technology, so the gas sensor 10 is extremely small relative to the smokestack 50 of the boiler.

As is clear from the state of installation in FIG. 3, the temperature measuring resistors of the gas sensor chips 100 and 100' are disposed on the base substrate so as to be on the side opposite from the direction wherein the exhaust gas flows in the smokestack 50.

Here the temperature within the smokestack rises to approximately 200° C. when the exhaust gas flows through the smokestack 50 of the boiler as indicated by the white arrow in the figure. Additionally, power is supplied to the heaters-cum-temperature measuring resistors 120 through the electrode lead pins 125 of the gas sensor chips 100 and 100' illustrated in FIG. 2, to increase the temperatures of the catalyst carrier portions to 280° C. The carbon monoxide (non-combusted gas) included in the exhaust gas that enters into the recessed portion 130 of the first gas sensor chip 100 on which the oxidation combustion catalyst 150 is supported is caused by heating to react with the oxidation combustion catalyst 150, to thereby combust. The heat that is produced in the porous silicon layer 140 through the combustion of the carbon monoxide propagates to the temperature measuring resistor 120 through the thin wall portion 113 of the gas sensor chip 100. As a result, there is a slight change in the resistance value of the temperature measuring resistor 120 of the first gas sensor chip 100 due to the increase in temperature based on this thermal conduction.

On the other hand, in the gas sensor chip 100', wherein there is no oxidation combustion catalyst 150 supported by the porous silicon layer 140, there is no increase in temperature due to combustion of carbon monoxide (non-combusted gas) in this way, and so there is no change in the resistance value of the temperature measuring resistor based thereon.

Consequently, sensing, through the Wheatstone bridge circuit that is structured by the electric wires (not shown) connected to the electrode lead pins 125, described above, the voltage values that are detected by each of the temperature measuring resistors in the first gas sensor chip 100 that is provided with the oxidation combustion catalyst 150 and the other gas sensor chip 100' that is not provided with the oxidation combustion catalyst 150 makes it possible to measure the increase in temperature that is produced when there is combustion of non-combusted gas due to the oxidation combustion catalyst 150, based on the change in the resistance values of both, without being affected by the change in temperature of the exhaust gas itself.

The relative comparisons of the amounts of heat produced in the gas sensor chip 100 that is provided with the oxidation combustion catalyst 150 and the gas sensor chip 100' that is not provided with the oxidation combustion catalyst 150 in this way cancels out the slight changes in temperature of the exhaust gas itself that always occur within a boiler smokestack, making it possible to detect only the amount of heat produced by the combustion of the carbon monoxide that is the non-combusted gas within the exhaust gas. The result is that it is possible to measure accurately the amount of the carbon dioxide constituent included within the exhaust gas within the boiler smokestack, making it possible to a optimize the combustion control through feeding this back to the boiler combustion control device, and, if the carbon monoxide constituent is extremely large, to determine that a problem has occurred; within the boiler itself, enabling a forced shutdown of the combustion within the boiler.

Additionally, because the gas sensor 10 is provided with a temperature measuring resistor 120 on the side that is opposite from the side wherein the exhaust gas flows, as described above, it is possible to avoid a reduction in the service life of the sensor, such as through corrosion of the electrodes or shorting of the interconnections, due to the temperature sensing portion contacting the gas to be measured, as with the conventional gas sensor, making it possible to detect the quantity of the carbon monoxide constituent accurately over an extended period of time even in a gas sensor 10 that is provided with gas sensor chips 100 and 100' that have been miniaturized through MEMS technology.

A modified example of the gas sensor chips 100 and 100' and of the gas sensor 10 according to the example of embodiment described above will be explained below. Note that those structures that are identical to those in the example of embodiment described above are assigned identical codes, and detailed explanations thereof are omitted.

A gas sensor chip 200 according to the modified example of the example of embodiment described above will be explained first. The gas sensor chip 200 according to this modified example has a groove 215 formed in the periphery of a temperature measuring resistor 220 for achieving thermal insulation of the temperature measuring resistor 220. Note that this groove 215 has a depth that reaches to the vicinity of the surface of the side of the base substrate 210 that is opposite from the temperature measuring resistance 220, through a silicon nitride layer 211.

A recessed portion 230, having an opening portion of a size corresponding to the temperature measuring resistor 220, is formed on the surface on the side of the base substrate 210 that is opposite from, and facing, the temperature measuring resistor 220, as with the example of embodiment described above. The bottom surface (the top surface in the figure) of the recessed portion 230 forms a thin wall portion 213, corresponding to the region in which the temperature measuring resistor 220 is formed.

Furthermore, in this gas sensor chip 200 according to the present modified example, the presence of this type of groove 215 means that the sideways peripheral surface of the recessed portion 230 also forms a thin wall portion 214 in cooperation with the groove 215 that is formed at the periphery of the temperature measuring resistor 220. A higher level of thermal insulation is achieved, relative to the surrounding base substrate 210, for the thin wall portions 213 and 214, and the temperature measuring resistor 220. The porous silicon layer 240 that is formed on the inside surface of the recessed portion 230, or in other words, on the inside surface of the thin wall portion 213 corresponding to the temperature measuring resistor 220 and the thin wall portion 214 corresponding to the groove 215, fulfills the role of the carrier for the oxidation combustion catalyst 215.

In this way, the thin wall portion 214 is formed not just in the area of the recessed portion 230 corresponding to the temperature measuring resistor 220, but also between the groove 215 and the side wall surface of the recessed portion 230, to not only make it difficult for the heat that is generated by the oxidation combustion catalyst 250 to propagate in the sideways direction of the base substrate 210, but also to cause efficient thermal propagation to the temperature measuring resistor 220, making it possible to measure more accurately the amount of heat generated by the carbon monoxide reacting with the oxidation combustion catalyst 250, to thereby enable a more accurate calculation of the amount of the carbon dioxide constituent within the gas.

A modified example of the gas sensor 10, set forth above, will be explained next. Note that those structures that are identical to those in the gas sensor 10 according to the example of embodiment set forth above are assigned corresponding codes, and detailed explanations thereof are omitted.

Figure 5:
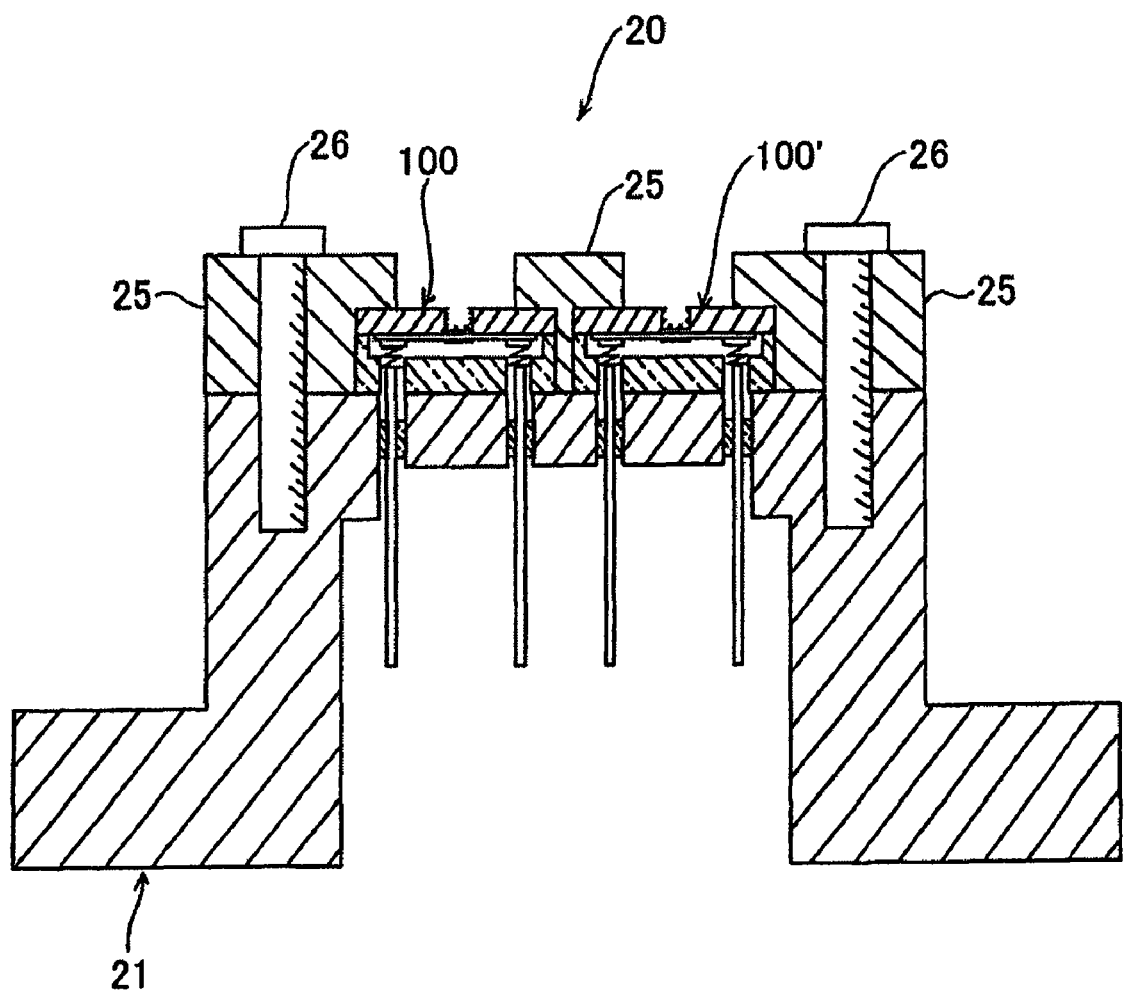
FIG. 5 is a cross-sectional diagram illustrating a modified example of the gas sensor illustrated in FIG. 2.

Instead of two gas sensor chips 100 and 100' being secured to a sensor supporting member 11 by an adhesive, as with the case of the gas sensor 10 set forth above, in the gas sensor 20 according to the present modified example, a chip holder 25, made from a material with superior thermal insulation, is attached to the sensor supporting member 21 by a fastener, such as a bolt 26, as illustrated in FIG. 5.

Figure 6:
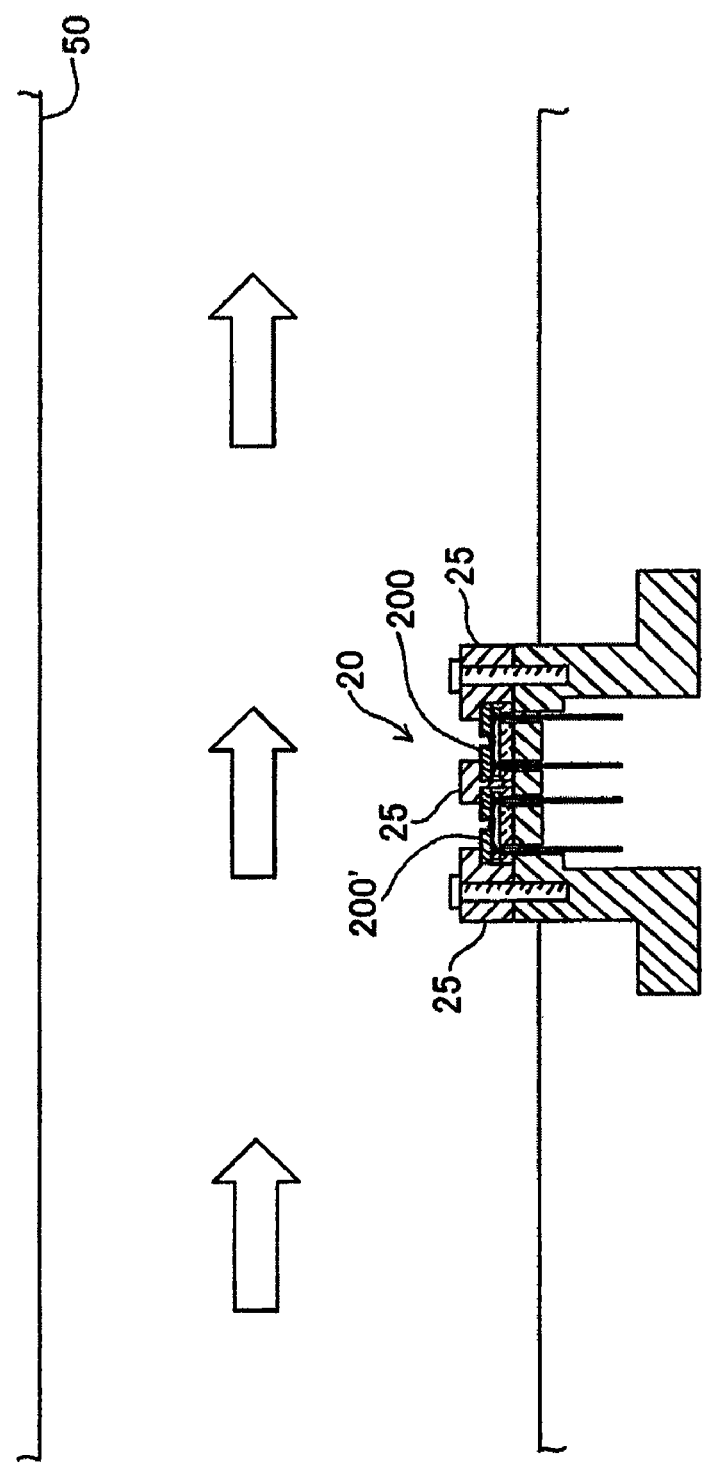
FIG. 6 is a cross-sectional diagram illustrating the state wherein the gas sensor illustrated in FIG. 5 is installed in a boiler smokestack.

Gas sensor chips 200 and 200' are attached to the sensor supporting member 21 by the chip holder 25 that has superior thermal insulation in this way, so that, as illustrated in FIG. 6, even if relatively large dust particles included in the exhaust gas (shown by the white arrow in the figure) in the smokestack 50 were to strike the gas sensor 20, when the gas sensor 20 is, for example, installed in a boiler smokestack 50, the gas sensor 20 will not break, and will not be adversely affected by the vibrations caused by pulsation of the exhaust gas.

In this way, with the gas sensor chip according to the present invention, the temperature measuring resistor is formed on the side of the base substrate that is opposite from the side wherein the gas flows. When measuring non-combusted gas in an exhaust gas flowing in a boiler smokestack there is no contact between the temperature sensing portion and the exhaust gas. Thus, there is no production of degradation in the temperature sensing portion, such as corrosion of the electrodes or shorting of the interconnections, such as described above. Because of this, it is possible to detect the amount of the carbon monoxide constituent stably over an extended period of time, even with a gas sensor chip that is extremely small through MEMS technology.

It is possible, for example, to optimize the combustion efficiency of the combustion equipment through feeding back the amount of the non-combusted gas constituent in the exhaust gas to the combustion control equipment of the boiler, and possible to detect promptly deterioration in the performance of the boiler itself.

The gas sensor provided with the gas sensor chip enables the detection of only that change in temperature due to the combustion of carbon monoxide, which is a non-combusted gas, included in the exhaust gas, without being affected by variations in the temperature of the exhaust gas itself or by variations in the ambient temperature, through comparing the output of a gas sensor chip that is provided with the oxidation combustion catalyst and the output of a gas sensor chip that is not provided with the oxidation combustion catalyst.

Furthermore, the durability of the gas sensor chip itself is increased through the temperature measuring resistor not coming into direct contact with the gas, thereby reducing the frequency of maintenance on the gas sensor.

Note that while the oxidation combustion catalyst described above was adhered to the gas sensor chip by performing sintering after impregnating the porous silicon layer with a catalyst fluid of platinum and palladium, the oxidation combustion catalyst may be adhered to the gas sensor chip without using this method through, for example, plating, sputtering, performing vapor deposition, or the like, of platinum, palladium, or the like, without forming a porous silicon layer on the inner peripheral surface of the recessed portion.

However, forming a porous silicon layer on the inner surface of the recessed portion and including the oxidation combustion catalyst within the porous silicon layer increases the surface area over which the gas makes contact with the catalyst. This increases the combustion temperature by that much, even given an identical constituent of non-combusted gas with in the gas. This makes it possible to measure the amount of the non-combusted gas constituent accurately.

Additionally, while the oxidation combustion catalyst may exhibit the effects of the present invention even when included in only the area of the porous silicon layer corresponding to the temperature measuring resistor, more preferably it may be included in the entirety of the porous silicon layer that is formed over the entirety of the inner surface of the recessed portion in the example and in the modified example.

Additionally, the groove in the gas sensor chip in the modified example set forth above was formed continuously so as to encompass the periphery of the temperature measuring resistor. However, a large number of holes having interior diameters that are equal to the width of the groove, and depths equal to the depth of the groove, may be formed in the same area continuously instead of the groove.

Furthermore, while carbon monoxide was described as the non-combusted gas in the example of embodiment and modified example set forth above, the present invention is not necessarily limited to detecting only carbon monoxide, but, of course, may also be applied to measuring the amount of other non-combusted gasses, such as oxygen and methane, within a gas.

As described above, with the conventional contact combustion-type carbon monoxide sensor, and the like, the gas to be measured would come into contact with the catalyst, and the heating phenomenon would be used to calculate the density of the gas by detecting the amount of heat produced directly using a temperature sensing portion.

In this conventional gas sensor, there were cases wherein a gas that is a harsh environment for the materials from which the sensor is constructed was selected as the gas to be measured, shortening the service life of the sensor depending on the type of gas measured, in, for example, the case of an exhaust gas within a boiler smokestack. Furthermore, the shorter the service life of the sensor, the more frequent the maintenance (or the greater the frequency with which the sensor was replaced), and thus there was a problem with ensuring operation and with operating cost.

This was caused by the structure of the conventional contact combustion-type gas sensor having the catalyst carrier being the heat producing portion, with the temperature sensing portion being structured so as to be in direct contact with the catalyst carrier in order to detect the heat production efficiently.

A gas sensor of this type of conventional structure is structured based on the normal approach for a sensor structural design, but these structural elements that produce the change in state (the catalyst carrier in the case of a gas sensor) and the structural elements that provide the sensing function (the temperature sensing portion in the case of a gas sensor) having the positional relationship wherein they are in direct contact is an extremely rational design concept from the perspective of linking so as to increase the so-called sensor sensitivity.

However, in the contact combustion-type sensor, naturally the catalyst medium is in direct contact with the gas to be measured. As a result, when a structure that is based on the rational design concept described above is used, then the temperature sensing portion also cannot avoid direct contact with the gas to be measured, and the corrosion, by the corrosive constituent included in the gas to be measured, due to the temperature sensing portion being in contact with the gas to be measured, reduces the service life of the sensor as a whole, and it was this shortcoming upon which the inventors of the present invention focused, and the technical significance is found in a complete solution for this shortcoming.

In addition, when viewed from a different perspective, when in a state wherein there is a trade-off between increased sensitivity of a particular sensor and an extended service life, it is not always just the sensor sensitivity that is of the top priority in an industrial application. In contemplation of this fact, there is also technical significance in the inventors of the present invention making it clear that the use of the so-called "backside structure" in the present invention, wherein the temperature sensing portion and the catalyst carrier are separated so that the temperature sensing portion is disposed in a position that does not contact the gas to be measured, as a structure capable of extending the service life of the sensor is an effective solution to the problem of the present invention, albeit slightly sacrificing sensor sensitivity.

That is, the critical focus of the present invention is a solution for the negative impact on the service life of the contact combustion-type sensor resulting from the conventional "rational design concept."

The invention claimed is:

1. A gas sensor chip comprising:
   a base substrate made from silicon;
   a temperature measuring resistor disposed on one surface of the base substrate and an electrode conducting electrically thereto;
   a recessed portion forming a thin wall portion of the base substrate on the opposite side of the base substrate facing the temperature measuring resistor, in the interval of the temperature measuring resistor;
   a porous silicon layer is formed on at least the surface of the thin walled portion of the inner surface of the recessed portion;
   an oxidation combustion catalyst supported by the porous silicon layer; and
   a glass mount connected to the temperature measuring resister side of the base substrate;
   wherein a gas flows on the side of the base substrate that is opposite from the surface in which the temperature measuring resistor is formed.

* * * * *